United States Patent [19]
Heitkamp et al.

[11] Patent Number: 5,980,738
[45] Date of Patent: Nov. 9, 1999

[54] POROUS POLYMERIC BIOSUPPORTS

[75] Inventors: Michael A. Heitkamp, Ballwin, Mo.; George C. Stow, Pensacola, Fla.

[73] Assignee: Monsanta Company, St. Louis, Mo.

[21] Appl. No.: 08/725,873

[22] Filed: Oct. 4, 1996

Related U.S. Application Data

[60] Provisional application No. 60/004,764, Oct. 4, 1995.

[51] Int. Cl.$^6$ .................................................... C12N 11/08
[52] U.S. Cl. ........................... 210/150; 210/617; 435/180
[58] Field of Search .................................. 210/615–617, 210/150, 151, 510.1; 435/180; 252/180; 502/402; 261/DIG. 72

[56] References Cited

U.S. PATENT DOCUMENTS

| | | | |
|---|---|---|---|
| 3,268,636 | 8/1966 | Angell | 264/51 |
| 3,327,031 | 6/1967 | Boyer et al. | 264/53 |
| 3,407,151 | 10/1968 | Overcashier et al. | 260/2.5 |
| 3,861,404 | 1/1975 | Changani | 131/269 |
| 4,009,105 | 2/1977 | Jeris | 210/107 |
| 4,070,426 | 1/1978 | Purvis | 264/54 |
| 4,165,281 | 8/1979 | Kuriyama | 210/17 |
| 4,415,454 | 11/1983 | Fuchs | 210/616 |
| 4,544,594 | 10/1985 | Li et al. | 428/92 |
| 4,552,810 | 11/1985 | Norota et al. | 428/398 |
| 4,567,718 | 2/1986 | Reischl et al. | 210/616 |
| 4,876,288 | 10/1989 | Herding et al. | 521/53 |
| 4,915,884 | 4/1990 | Capdeville et al. | 264/15 |

(List continued on next page.)

FOREIGN PATENT DOCUMENTS

| | | | |
|---|---|---|---|
| 0121851 A2 | 3/1984 | European Pat. Off. | |
| 0186125 A2 | 7/1986 | European Pat. Off. | C12N 11/08 |
| 0209790 A2 | 7/1986 | European Pat. Off. | |
| 0467528 A2 | 1/1992 | European Pat. Off. | C08J 9/28 |
| 0472249 A2 | 2/1992 | European Pat. Off. | C02F 3/10 |
| 0696611 A2 | 2/1996 | European Pat. Off. | C08J 9/00 |
| 0696612 A2 | 2/1996 | European Pat. Off. | C08J 9/228 |
| 63-232393 | 9/1988 | Japan | H05K 3/46 |
| 7-179645 | 7/1995 | Japan | C08J 9/16 |
| 6603754 | 9/1996 | Netherlands . | |
| 1034076 | 6/1966 | United Kingdom . | |
| 1082661 | 9/1967 | United Kingdom | C02C 1/04 |
| 1318964 | 5/1973 | United Kingdom | C08G 53/08 |
| 2230278 A | 10/1990 | United Kingdom . | |
| WO 92/18609 | 10/1992 | WIPO | C12M 1/40 |
| WO 93/01231 | 1/1993 | WIPO | C08J 9/26 |
| WO 94/14712 | 7/1994 | WIPO | C02F 3/10 |
| WO 95/23768 | 9/1995 | WIPO | C05F 3/10 |

OTHER PUBLICATIONS

Tsubone, Ogaki, Yoshiy, Takahashi; Effect of biomass entrapment and carrier properties on the performance of an air–fluidized–bed biofilm reactor; *Water Environment Research*; vol. 64, No. 7; pp. 884–889; Nov./Dec. 1992.

Edwards, Adams, Heitkamp; Laboratory–scale evaluation of aerobic fluidized bed reactors for the biotreatment of a synthetic, high–strength chemical industry waste stream; *Water Enviroment Research*; vol. 66, No. 1; pp. 70–83; Jan./Feb. 1994.

Heitkamp, Camel, Reuter, Adams; Biodegradation of p–Nitrophenol in an Aqueous Waste Stream by Immobilized Bacteria; *Applied and Enviromental Microbiology*; vol. 56, No. 10; pp. 2967–2973; Oct. 1990.

*Primary Examiner*—Thomas G. Wyse
*Attorney, Agent, or Firm*—Jon H. Beusen; Arnold, White & Durkee

[57] ABSTRACT

Porous biosupports for the support of microorganisms which are used in the biotreatment of an aqueous waste stream comprising a polymeric material and, optionally, fiber reinforcement, adsorbent material and/or inorganic filler wherein the biosupport has a specific gravity greater than the specific gravity of water and pores of sufficient diameter to enable microorganisms to readily colonize within the pores, a process for preparing same, and processes for biodegrading an aqueous waste stream containing organic contaminants utilizing the porous biosupports.

40 Claims, 7 Drawing Sheets

U.S. PATENT DOCUMENTS

| | | | |
|---|---|---|---|
| 4,960,549 | 10/1990 | Brooks et al. | 264/45.5 |
| 4,983,299 | 1/1991 | Lupton et al. | 210/617 |
| 5,211,848 | 5/1993 | Friday et al. | 210/611 |
| 5,217,616 | 6/1993 | Sanyal et al. | 210/617 |
| 5,229,209 | 7/1993 | Gharapetian et al. | 428/403 |
| 5,254,254 | 10/1993 | Shin et al. | 210/611 |
| 5,288,635 | 2/1994 | Adams et al. | 435/262.5 |
| 5,294,384 | 3/1994 | David et al. | 264/37 |
| 5,342,646 | 8/1994 | Kleese et al. | 427/2.1 |
| 5,397,755 | 3/1995 | Parker et al. | 502/7 |
| 5,403,487 | 4/1995 | Lodaya et al. | 210/610 |

POROUS POLYMERIC BIOSUPPORTS

This application claims priority of U.S. provisional application No. 60/004,764, which filed on Oct. 4, 1995.

BACKGROUND OF THE INVENTION

This invention relates to porous polymeric biosupports, particularly porous nylon biosupports. In one aspect, this invention relates to use of porous polymeric biosupports in processes for biodegradation of aqueous waste streams containing organic contaminants. In another aspect, this invention relates to use of porous polymeric biosupports in packed bed and fluidized bed reactors for biotreatment of aqueous waste streams. In a further aspect, this invention relates to the process for preparing the porous polymeric biosupports.

Commercial utilization of immobilized bacteria technology (IBT) for cost-effective biological treatment of chemical wastes has been increasing. IBT utilizes highly selected, chemical-degrading bacteria in bioreactors designed to provide optimal conditions for microbial activity.

In IBT, biosupports are hosts for the bacteria which degrade toxic or polluting chemicals in waste streams into environmentally harmless products. This is usually done by flowing the waste stream through a reactor vessel containing the bacteria on a biosupport media.

Chemical degrading bacteria immobilized in bioreactors have been shown to achieve exceptional performance for the biotreatment of chemical industry wastes. Use of IBT in fluidized bed reactors (FBRs) and packed bed reactors (PBRs) achieve high rates of chemical removal, tolerate harsh conditions, survive dormancy, tolerate surge loadings, and produce lower levels of biological solids than conventional waste treatment technologies.

The biosupports which are typically used in commercial scale bioreactors are predominantly sand, granular activated carbon (GAC) particles and porous inorganic particles such as diatomaceous earth, alumina oxide and sintered glass. Although these biosupports, also known as biocarriers, are commercially available and have been well-proven as supports for chemical-degrading bacteria, they all have some disadvantages. The GAC and inorganic biosupports are expensive and experience attrition of 5–20% per year. In addition, the removal of excess biomass from these biosupports is problematic since their high density and fragility make vigorous back-flushing or mechanical biomass separation difficult. Sand is affordable and non-fragile, but requires a significantly longer period of time for microbial colonization (slower startup) and lacks the advantage of chemical adsorption as a supplementary removal mechanism. In addition, microorganisms on sand are more prone to performance failure and slow recovery after physical or chemical upsets.

Lodaya et al (U.S. Pat. No. 5,403,487) has disclosed the use of microporous synthetic resinous materials, including nylon, as biosupports for use in treating aqueous waste streams in aerated packed bed reactors. The microporous synthetic resinous materials of Lodaya et al have a density less than the density of water, i.e. float in the reactor, and therefore require a screen to hold the resin particles in place. The density of the microporous synthetic resinous materials of Lodaya et al creates the significant problem of not being able to handle biofouling and biomass control in the packed bed reactor. The packed bed reactor of Lodaya et al also requires use of a recycle stream. In addition, the microporous synthetic resinous materials of Lodaya et al cannot be used in fluidized bed reactors because they float.

A biosupport material which solves the problems of the commercially available biosupports and of materials such as those disclosed in Lodaya et al would be highly desirable. It has now been found that the porous polymeric biosupports of the invention solve the above-described problems. Specifically, the porous polymeric biosupports of the invention have the following advantages: (1) high porosity permitting rapid and heavy colonization by inoculated bacteria, (2) large pore sizes and open structure promoting higher levels of microorganism growth inside the biosupport and resulting in greater tolerance to upsets, less biomass loss during fluidization and higher overall performance, (3) high physical strength eliminating attrition, (4) inert to most chemicals and waste streams, (5) density slightly greater than the density of water eliminating the problems of Lodaya et al and permitting simple, cost-effective fluidization by air injection to control biomass in PBRs, (6) high rigidity providing good abrasion of excess biomass during fluidization, (7) chemical biodegradation rates equal to or exceeding commercially available biosupports, and (8) production process allowing flexibility in size, density, porosity and composition of the biosupports.

The porous polymeric biosupports of the invention also have the advantage of utilizing waste polymer or recycle polymer as feedstock. This utilization of waste or recycle polymer is an environmentally friendly process resulting in waste recycling and reduction.

SUMMARY OF THE INVENTION

It is an object of the invention to provide a porous polymeric biosupport having a density greater than the density of water and open pores of sufficient diameter to enable microorganisms to readily colonize within the pores. It is a further object of the invention to provide a porous polymeric biosupport which is essentially free from attrition during operation of a fluidized bed or packed bed bioreactor. It is yet a further object of the invention to provide a porous polymeric biosupport which is relatively inexpensive. It is still a further object of the invention to provide a porous polymeric biosupport to which can be incorporated an adsorbent material for use as a supplementary removal mechanism to enhance biodegradation and maintain a high quality effluent, and fiber reinforcement for improved strength.

According to the invention, a porous biosupport for the support of microorganisms which is used in the biotreatment of an aqueous waste stream is provided which comprises a polymeric material comprising a thermoplastic polymer and, optionally, fiber reinforcement, adsorbent material and/or inorganic filler, wherein the biosupport has a specific gravity greater than the specific gravity of water and pores of sufficient diameter to enable microorganisms to colonize within the pores.

Further according to the invention, a process for biodegrading an aqueous waste stream containing organic contaminants is provided which comprises inoculating a bed of particles of the biosupport of the invention with an inoculum of a culture of microorganisms capable of biodegrading the organic contaminants and contacting the aqueous waste stream containing organic contaminants with the microorganisms on the biosupport for a sufficient time to degrade the organic contaminants. In one embodiment of the invention, the process is conducted in a packed bed reactor. In another embodiment of the invention, the process is conducted in a fluidized bed reactor.

Still further according to the invention, a process for preparing the porous biosupport of the invention is provided which comprises extruding in a non-vented extruder a composition comprising a polymeric material comprising nylon and, optionally, fiber reinforcement and/or adsorbent material, wherein the composition being extruded has a moisture content of about 0.1–about 7 wt. %, and pelletizing the extrudate from the extruder.

DESCRIPTION OF ILLUSTRATIVE EMBODIMENTS

A first embodiment of the invention relates to a porous biosupport for the support of microorganisms for the biotreatment of an aqueous waste stream containing organic contaminants comprising (a) 40–100 wt. % of a polymeric material comprising a polymer selected from the group consisting of nylon, thermoplastic polyester, ethylene-vinyl acetate copolymer, ethylene-vinyl alcohol copolymer, polysulfone, polyolefin, polyvinyl chloride, polycarbonate, polyimide, polyetheretherketone, polyphenylene sulfide, cellulose ester plastics, polyvinyl butyral, styrenic polymers, rigid, thermoplastic polyurethanes, and mixtures thereof, (b) 0–60 wt. % of a fiber reinforcement, (c) 0–60 wt. % of an adsorbent material, and (d) 0–40 wt. % of an inorganic filler, wherein the sum of the amounts of fiber reinforcement, adsorbent material and inorganic filler in the biosupport is 0–60 wt. %, and the biosupport has a specific gravity greater than the specific gravity of water and pores of sufficient diameter to enable microorganisms to colonize within the pores.

The preferred polymeric materials for use in the biosupport of the invention comprise a polymer selected from the group consisting of nylon, thermoplastic polyester, ethylene-vinyl alcohol copolymer, polysulfone, polyvinyl chloride, polycarbonate, polyimide, polyetheretherketone, polyphenylene sulfide, cellulose ester plastics, polyvinyl butyral, styrenic polymers, rigid, thermoplastic polyurethanes, and mixtures thereof because the polymers have specific gravities greater than 1.0. More preferred polymeric materials for use in the biosupport of the invention comprise a polymer selected from the group consisting of nylon, thermoplastic polyester, and mixtures thereof because of the availability of recycle or waste material. The most preferred polymer for use in the polymeric materials of the invention is nylon because of excellent results obtained therewith. In addition to the polymer, the polymeric material of the invention can also contain polymers other than those listed above and fillers, particularly inorganic fillers. When a polymer with a specific gravity less than 1.0, e.g. a polyolefin, is used the polymeric material must contain other materials or the biosupport must contain an adsorbent material, a fiber reinforcement and/or an inorganic filler such that the specific gravity of the polymeric material is greater than 1.0. For example, if a polyolefin is used then either an additional polymer having a specific gravity greater than 1.0 or an adsorbent material, a fiber reinforcement and/or an inorganic filler must also be used.

Suitable nylon polymers for use in the biosupport include any readily available type of nylon, particularly nylon 6, nylon 6,6, nylon 4,6, nylon 11, nylon 12, nylon 6,9, nylon 6,10 and blends or copolymers thereof. The currently preferred nylon polymers are nylon 6 and nylon 6,6 because of their cost and availability. Of particular interest for use in the biosupports of the invention are waste nylon materials including, but not limited to, manufacturing wastes, off-spec product, and cuttings from the manufacture of nylon carpet. In addition, nylon for use in the invention can be derived from used nylon carpet which is obtained according to the process described in U.S. Pat. No. 5,294,384, which is incorporated by reference herein. The nylon derived from used carpet which is processed without separating the carpet into its component parts will also contain at least one polyolefin (derived from the backing), a styrene-butadiene rubber (SBR) (used as an adhesive) and, optionally, an inorganic filler. Nylon for use in the invention can also be derived from other recycled nylon products such as molded nylon objects which can be reprocessed. Such nylon products may contain fiber reinforcement and inorganic fillers. The use of waste or recycle nylon as the source of nylon in the biosupports of the invention is an environmentally friendly utilization of waste material which would otherwise have to be disposed of, such as by landfilling.

Suitable thermoplastic polyesters for use in the biosupport are readily available and include polymers described in the *Encyclopedia of Polymer Science and Engineering*, 2nd ed., Vol. 12, pp. 1–75 and 217–256 (1988), which is incorporated by reference herein. Particularly useful thermoplastic polyesters include polyethylene terephthalate (PET) and polybutylene terephthalate (PBT). In particular, waste or recycle PET and PBT, including material derived from used polyester carpet, are suitable sources of polyester material. The polyester derived from used carpet which is processed without separating the carpet into its component parts will also contain material derived from the backing, e.g. a polyolefin, an adhesive such as SBR and, optionally, an inorganic filler.

The polyvinyl chloride for use in the biosupport can be a homopolymer or it can be a copolymer of vinyl chloride and vinyl acetate which typically contains 85–97% of the chloride monomer.

The polyolefins for use in the biosupport include homopolymers of ethylene and propylene, and copolymers of ethylene and propylene with another olefin, e.g. ethylene/ propylene and ethylene/hexene copolymers. Used polypropylene carpet is a suitable source of polypropylene. The polypropylene derived from used carpet which is processed without separating the carpet into its component parts will also contain material derived from the backing, an adhesive such as SBR and, optionally, an inorganic filler.

The polysulfones for use in the biosupport are readily available and include polymers described in the *Encyclopedia of Polymer Science and Engineering,* 2nd ed., Vol. 13, pp. 196–211 (1988), which is incorporated by reference herein. The polysulfones for use in the biosupports of the invention include polyethersulfones.

The polycarbonates for use in the biosupport are readily available and include polymers described in the *Encyclopedia of Polymer Science and Engineering,* 2nd ed., Vol. 11, pp. 648–718 (1988), which is incorporated by reference herein.

The polyimides for use in the biosupport are readily available and include polymers described in the *Encyclopedia of Polymer Science and Engineering,* 2nd ed., Vol. 12, pp. 364–383 (1988), which is incorporated by reference herein. The polyimides for use in the biosupports of the invention include polyetherimides.

The polyetheretherketones for use in the biosupport are readily available and include polymers described in the *Encyclopedia of Polymer Science and Engineering,* 2nd ed., Vol. 12, pp. 313–320 (1988), which is incorporated by reference herein.

Suitable polyphenylene sulfide for use in the biosupport are readily available and include polymers described in the *Encyclopedia of Polymer Science and Engineering,* 2nd ed., Vol. 11, pp. 531–557 (1988), which is incorporated by reference herein.

The cellulose ester plastics for use in the biosupport are readily available and include polymers described in the *Encyclopedia of Polymer Science and Engineering,* 2nd ed., Vol. 3, pp. 181–200 (1988), which is incorporated by reference herein. Particularly useful cellulose ester plastics are cellulose acetate, cellulose acetate butyrate and cellulose acetate propionate.

The polyvinyl butyral materials for use in the biosupport are commercially available and have a hydroxyl content expressed as percent poly (vinyl alcohol) of up to 20%. The ethylene-vinyl acetate and ethylene-vinyl alcohol copolymers for use in the biosupports of the invention are commercially available.

Styrenic polymers, as used herein, include polystyrene, rubber-modified polystyrene or high impact polystyrene (HIPS), acrylonitrile-styrene copolymers (SAN), rubber-modified acrylonitrile-styrene copolymers (ABS), styrene-maleic anhydride copolymers (SMA), styrene-methyl methacrylate copolymers, and acrylate-styrene-acrylonitrile copolymers (ASA). The styrenic polymers for use in the biosupport are readily available and include polymers described in the *Encyclopedia of Polymer Science and Engineering,* 2nd ed., Vol. 16, pp. 62–97, and Vol. 1, pp. 388–426 and 452–464 (1988), which are incorporated by reference herein.

Suitable polyurethane materials for use in the biosupport are commercially available and are rigid, thermoplastic materials that are capable of producing open-cell structures.

Suitable inorganic fillers for use in the biosupports of the invention include carbonates such as calcium carbonate and barium carbonate, silicates such as clay (kaolin), calcium silicate, mica, talc and wollastonite, sulfates such as calcium sulfate and barium sulfate, and oxides such as silicon dioxide and titanium dioxide. The currently preferred fillers are calcium carbonate, calcium sulfate, kaolin, mica, talc and wollastonite.

The amount of polymeric material present in the biosupports of the invention is broadly 40 to 100 wt. % of the biosupport. The preferred biosupports of the invention contain 40 to about 80 wt. % polymeric material with the remainder being fiber reinforcement, adsorbent material and/or inorganic filler. It is more preferred that the biosupports of the invention contain at least some fiber reinforcement to improve the physical strength of the biosupport.

It is currently preferred that the polymeric material consist essentially of nylon. If the polymeric material contains other components, the amount of nylon present is about 35 to about 95 wt. %, preferably about 40 to about 85 wt. %, of the polymeric material. When the source of nylon is used carpet, which typically contains an inorganic filler in the SBR adhesive used, the polymeric material comprises 35 to 67 wt. % nylon, 8 to 21 wt. % polyolefin, 5 to 29 wt. % SBR and 10 to 40 wt. % inorganic filler.

The fiber reinforcement for use in the biosupports of the invention are fibers selected from the group consisting of glass, carbon, aramid, fiber-forming inorganic material selected from alumina, silica, boron, boron nitride, boron carbide, silicon carbide or alumino-silicate, and mixtures thereof. The currently preferred fiber reinforcement is glass fiber or carbon fiber due to cost, performance and availability, with glass fiber being most preferred. The preferred form of the fiber reinforcement is chopped fibers.

The adsorbent material for use in the biosupports of the invention are selected from the group consisting of carbon (including charcoal, activated carbon, graphite and carbon black), ion exchange resins, zeolites and mixtures thereof. The currently preferred adsorbent material is carbon, specifically charcoal or activated carbon.

The amount of fiber reinforcement present in the biosupports of the invention is broadly 0 to 60 wt. % of the biosupport, preferably about 5 to about 50 wt. %, and most preferably about 15 to about 40 wt. %. The amount of adsorbent material present in the biosupports of the invention is broadly 0 to 60 wt. % of the biosupport, preferably about 2 to about 50 wt. %, and more preferably about 3 to about 30 wt. %. The amount of inorganic filler present in the biosupports of the invention is broadly 0 to 40 wt. % of the biosupport, preferably about 5 to about 30 wt. %, and more preferably about 10 to about 25 wt. %. The total amount of fiber reinforcement, adsorbent material and inorganic filler in the biosupports of the invention shall not exceed 60 wt. %.

The polymeric material of the biosupports of the invention can further comprise a polymeric additive material wherein the additive material contains one or more of fiber reinforcement, adsorbent material, inorganic fillers, and polymeric material in addition to a plastic or rubber material not suitable as the primary polymeric material of the biosupport. Examples of plastic or rubber materials which can be present in the polymeric additive material but which are not suitable as the primary polymeric material of the biosupport include polybutadiene and rubbery copolymers thereof, e.g. styrene-butadiene rubber (SBR), acrylic polymers, polyphenylene oxide-based resins (PPO), and fiberglass reinforced plastics, particularly material recycled from automobiles, which contain, for example, crosslinked polyesters. A particularly suitable source of a rubbery polymeric additive is recycled used tires. Used tires contain, in addition to a rubber material such as SBR, materials including carbon black, fiber reinforcement, and polyester fibers. The polymeric additive material optionally contains other additives such as antioxidants, stabilizers, coupling agents, etc. which are not classified as fiber reinforcement, adsorbent material or inorganic fillers.

The percentage of plastic or rubber material present in the polymeric additive will determine the level of polymer additive which can be incorporated into the biosupport. The upper limit of the amount of polymeric additive is that amount above which will cause problems in production of the biosupport and will depend on the specific plastic or rubber material and its rheological and other pertinent properties. Generally, the upper limit will be that amount in which the amount of plastic or rubber material plus the amount of any additives other than fiber reinforcement, adsorbent material and inorganic filler present is up to about 30 wt. %, preferably up to about 15 wt. %, and more preferably about 10 wt. % of the biosupport.

Acrylic polymers, as used herein, include poly (methylmethacrylate), rubber-modified poly (methylmethacrylate), poly(methylacrylate), poly (ethylacrylate), poly(butylacrylate) and poly (ethylmethacrylate). Polyphenylene oxide-based resins, particularly blends of polyphenylene oxide with impact polystyrene, such as HIPS, are readily available.

The polymeric materials or polymeric additive materials utilized in the biosupports of the invention cannot contain an amount of any stabilizer, antioxidant, etc. which when incorporated in the biosupport would prevent the biosupport from being innoculated or from supporting microorganisms when used in immobilized bioreactors.

The biosupports of the invention are substantially open-cell materials, i.e. having open pores, and have a specific gravity greater than the specific gravity of water. The specific gravity of the biosupport has to be great enough that inoculated biosupport particles are not buoyant in the immobilized bacteria bioreactor during normal operation or during aeration or fluidization used for biomass control. Preferably, the specific gravity of the biosupports of the invention is greater than 1.1. The specific gravity of the biosupport can be readily controlled by varying the composition of the biosupport, i.e. the type and amount of polymeric material, fiber reinforcement and adsorbent material, and the process conditions under which the biosupports are extruded, e.g. concentration of water or foaming agent. The specific gravity of the biosupports of the invention enable the biosupports to be utilized in both fluidized bed and packed bed reactors. In FBRs, the specific gravity of the biosupport particles enables the biosupport particles to be fluidized during operation. In PBRs, the specific gravity of the biosupport particles enables the biosupport particles to be sufficiently mixed for biomass control in the reactor using air injection. The specific gravity of the biosupports of the invention is controlled such that the specific gravity is less than the specific gravity at which it is no longer practical to fluidize or sufficiently mix a bed of the biosupport particles. It is currently preferred that the specific gravity of the biosupport particles is below about 3, more preferably below about 2.

The biosupports of the invention have pores of sufficient diameter to enable microorganisms to colonize within the pores. Typical microorganisms have a diameter or thickness of 0.5–5 $\mu$m, such as about 1–2 $\mu$m, and a length of 2–4 $\mu$m. Therefore, biosupports having pore sizes larger than the size of the microorganisms are particularly useful. Generally, microorganisms require a pore diameter of at least 4 $\mu$m to have access to the pore. The biosupports of the invention were analyzed to determine pore sizes using mercury intrusion porosimetry and scanning electron microscopy. Mercury intrusion porosimetry is used to determine pore sizes in the range of 1 $\mu$m to about 390 $\mu$m. Scanning electron microscopy is used to qualitatively determine pore sizes of greater than 390 $\mu$m. It is clear from analyzing the micrographs (see Example 6) that the biosupports of the invention can be produced with external pore sizes, i.e. pore openings, of up to 700 $\mu$m and internal openings of up to 3.9 mm in length. The biosupports of the invention are particularly useful because they have external pores within the range of 1 $\mu$m to about 700 $\mu$m, preferably within the range of 1 $\mu$m to about 420 $\mu$m, and internal openings typically of up to about 800 to about 1200 $\mu$m in length. As the range of pore sizes is used herein, the biosupports of the invention can have pores that are smaller than 1 $\mu$m and larger than those set forth above. For pore sizes between 1 $\mu$m and 390 $\mu$m, the biosupports of the invention have a median pore diameter (based on volume) of at least about 40 $\mu$m, preferably at least about 50 $\mu$m, and most preferably at least about 70 $\mu$m. The actual median pore diameter of the biosupports of the invention will typically be larger due to the number of pores of diameter greater than 390 $\mu$m.

The biosupports of the invention can also be characterized via the cumulative pore volume and cumulative pore area. The cumulative pore volume or pore volume (for pore sizes greater than about 1 $\mu$m and up to 390 $\mu$m) of the biosupport particles is preferably at least 0.2, more preferably at least about 0.3, and even more preferably about 0.3 to about 1.0, mL/g biosupport. The cumulative pore area or pore area (for pore sizes greater than about 1 $\mu$m and up to 390 $\mu$m) of the biosupport particles is preferably at least 0.025, more preferably at least 0.03, $m^2$/g biosupport. As with the pore diameter, the actual cumulative pore volume and cumulative pore area will typically be larger due to the number of pores of diameter greater than 390 $\mu$m.

A second embodiment of the invention relates to a process for biodegrading an aqueous waste stream containing organic contaminants comprising inoculating a bed of particles of a biosupport with an inoculum of a culture of microorganisms capable of aerobically biodegrading the organic contaminants, and contacting the aqueous waste stream containing organic contaminants with the microorganisms on the biosupport for a sufficient time to degrade the organic contaminants; wherein the biosupport is as defined above. The biodegradation process can be conducted in any suitable immobilized bacteria bioreactor, particularly a fluidized bed or packed bed reactor. Suitable immobilized bacteria bioreactors also include in-situ biotreatment zones useful in in-situ bioremediation processes. An example of such an in-situ bioremediation process is described in U.S. Pat. No. 5,398,756, which is incorporated herein by reference. The biodegradation can be conducted aerobically or anaerobically depending on the specific organic contaminants and the microorganisms selected. It is currently preferred that the process be conducted aerobically due to applicability of aerobic biodegradation to a wide variety of organic contaminants.

A third embodiment of the invention relates to a process for treatment of an aqueous waste stream containing organic contaminants comprising passing the aqueous waste stream through a packed bed reactor, the packed bed reactor containing a packed bed of biosupport particles supporting microorganisms capable of biodegrading the organic contaminants, by a process in which the aqueous waste stream is oxygenated by introducing oxygen into the feed end of the packed bed reactor, thereby to subject the organic contaminants in the oxygenated aqueous waste stream to aerobic biodegradation and to produce a purified aqueous effluent; wherein the biosupport is as defined above.

The process can be conducted in conventional immobilized bacteria packed bed reactors which are well known to those skilled in the art, such as the one described in Heitkamp et al, "Biodegradation of p-Nitrophenol in an Aqueous Waste Stream by Immobilized Bacteria", *Appl. Environ. Microbiol.*, October 1990, pp. 2967–2973, which is incorporated by reference herein.

A fourth embodiment of the invention relates to a process for treatment of an aqueous waste stream containing organic contaminants comprising passing the aqueous waste stream through a fluidized bed reactor, the fluidized bed reactor including a recycle line and containing a fluidized bed of biosupport particles supporting microorganisms capable of biodegrading the organic contaminants, by a process in which the feed to the fluidized bed reactor is oxygenated, thereby to subject the organic contaminants in the oxygenated feed to aerobic biodegradation and to produce a purified aqueous effluent, wherein the feed to the fluidized bed reactor comprises a recycle stream of a portion of the effluent and the aqueous waste stream and the feed is oxygenated by dissolving oxygen in the recycle stream, the aqueous waste stream or the feed to through a fluidized bed reactor, the fluidized bed reactor including a recycle line and containing a fluidized bed of biosupport particles supporting microorganisms capable of biodegrading the organic contaminants, by a process in which the feed to the fluidized bed reactor is oxygenated, thereby to subject the organic contaminants in the oxygenated feed to aerobic biodegradation and to produce a purified aqueous effluent, wherein the feed to the fluidized bed reactor comprises a recycle stream of a portion of the effluent and the aqueous waste stream and the feed is oxygenated by dissolving oxygen in the recycle stream, the aqueous waste stream or the feed to the fluidized bed reactor at a point external to the fluidized bed; wherein the biosupport is as defined above.

The process can be conducted in conventional immobilized bacteria fluidized bed reactors which are well known to those skilled in the art, such as the one described in Edwards et al, "Laboratory-scale evaluation of aerobic fluidized reactors for the biotreatment of a synthetic, high-strength chemical industry waste stream", *Water Environ. Res.*, Vol. 66, No. 1, pp. 70–83 (January/February 1994) and U.S. Pat. No. 5,540,840 which issued Jul. 30, 1996, both of which are incorporated by reference herein.

A fifth embodiment of the invention relates to a process for preparing the porous biosupport of the invention comprising extruding in a non-vented extruder a composition comprising:

(a) 40–100 wt. % of a polymeric material comprising nylon, (b) 0–60 wt. % of a fiber reinforcement, (c) 0–60 wt. % of an adsorbent material, and (d) 0–40 wt. % of an inorganic filler, the sum of the amounts of fiber reinforcement, adsorbent material and inorganic filler in the biosupport is 0–60 wt. %, in the presence of about 0.2 to about 5 wt. % (based on the weight of the total composition) of water, a foaming agent or mixtures thereof, and pelletizing the extrudate from the extruder; wherein the biosupport has a specific gravity greater than the specific gravity of water and pores of sufficient diameter to enable microorganisms to colonize within the pores.

Water and/or the foaming agent present in the composition being extruded is broadly about 0.1 to about 7, preferably about 0.1 to about 5, more preferably about 0.1 to about 2, and most preferably about 0.2 to about 1, wt. % based on the weight of the total composition being extruded. The compound present in the composition being extruded which causes foaming and results in formation of the porous biosupport is water, a foaming agent or a mixture of water and a foaming agent.

Foaming agents, or blowing agents, are converted to gas during processing, i.e. extrusion, and the gas thus evolved creates the porous structure in the biosupport. This structure is influenced by the type and amount of foaming agent selected, the type of gas evolved and its solubility, the method of compounding/extrusion used, temperatures and pressures involved in processing, and the melt viscosity of the material being extruded. In the extrusion process for preparing the porous biosupports of the invention, water functions as a foaming agent.

Examples of suitable foaming agents include, but are not limited to, fluorinated aliphatic hydrocarbons such as chlorofluorocarbons, 1,1-azobisformamide (ABFA), p,p'-oxybis(benzenesulfonyl hydrazide) (OBSH), p-toluene sulfonyl semicarbazide (TSSC), trihydrazine triazine (THT), 5-phenyltetrazole (5-PT), sodium bicarbonate and mixtures thereof.

The composition to be extruded is prepared by mixing or blending the composition in any conventional polymer compounding blender. The temperature and pressure used in the extruder will depend on the particular material being extruded and will be readily apparent to those of ordinary skill in the art. In addition, the type and size of extruder used will be readily apparent to those of ordinary skill in the art. A single screw extruder is currently preferred.

The biosupport pellets produced can have any size and shape such as will allow them to be randomly packed in a packed bed reactor or fluidized in a fluidized bed reactor. The cross-section of the biosupport pellets will have the shape of the particular die used during extrusion, e.g. circular, rectangular, square, etc. The length of the biosupport pellets is determined by how the extrudate is cut or chopped. The biosupport pellets preferably have an effective diameter and or length such that the pellets have a desired size of greater than a No. 10 Sieve (U.S. A. Sieve Series-ASTM E-11-70, 2.0 mm), preferably greater than a No. 7 Sieve (U.S. A. Sieve Series-ASTM E-11-70, 2.8 mm). The maximum size of the biosupport pellets is that size which is no longer capable of being adequately fluidized or mixed in a bioreactor or which have a particle surface area to pore area ratio such that the pores are ineffective in enhancing the biodegradation in the bioreactor. A typical shape for the biosupports of the invention is cylindrical. For example, a typical extruded porous biosupport of the invention will have a cylindrical shape with a diameter of about 0.25–about 1.3 cm, preferably about 0.25–about 0.6 cm, and a length of about 0.6 cm–about 1.3 cm.

EXAMPLES

The chemicals used in the examples are as follows. p-Nitrophenol (PNP) having a purity >99% was obtained from Aldrich Chemical Co. (Milwaukee, Wis.). Standard plate count (SPC) agar and plating agar was obtained from Difco Laboratories (Detroit, Mich.). Yeast extract was obtained from Sigma Chemical Company (St. Louis, Mo.). Trypticase Soy Agar was obtained from Becton Dickinson and Company (Cockeysville, Md.). Inorganic chemicals were purchased from Fisher Scientific (Fair Lawn, N.J.).

Nylon was obtained from Monsanto Company. Diatomaceous earth (type R635) was obtained from the Manville Company. Activated coconut carbon was obtained from Charcoal Filtration Co. (Inglewood, Calif.).

PNP concentrations were determined spectrophotometrically by measuring optical absorbance at 414 nm. A linear relationship was observed between PNP absorbance and concentrations of PNP ranging from 0.5 to 35 mg/L. The pH of samples and standards was adjusted to above 8.0 using identical volumes of concentrated sodium hydroxide (2.5 N) in order to assure complete chromophore formation by the PNP. The absorbance of samples and standards was measured in 96-well microtiter plates using a Titertek Multiskan MCC/340 automatic plate reader (Flow Laboratories, Mclean, Va.). Effluent samples were collected with a pipette from each column and filtered through a 0.45 $\mu$m Acrodisc 25 syringe filter (Gelman Sciences, Ann Arbor, Mich.) prior to chemical analysis.

Porosity analyses were conducted as follows. Pore size distribution for the porous biosupports was determined by mercury intrusion porosimetry. Samples were placed into a penetrometer test cell which was then evacuated and filled with mercury. The diameter of the pores was calculated from the pressure required to force mercury into the porous biosupport particles. This pore diameter calculation assumes a circular cross-section for the pores. The samples were analyzed over the full instrument range, 0.46 psia (390 $\mu$m diameter) to 60,000 psia (30 Angstrom diameter). Scanning electron micrographs were used to determine the presence of pore sizes greater than 390 $\mu$m. Samples for scanning electron microscopy (SEM) were rinsed in a buffered solution (0.1 M sodium cacodylate, pH=7.4), fixed in 2% glutaraldehyde and stored in a refrigerator until analyzed. The fixed samples were warmed to room temperature, rinsed in the sodium cacodylate buffer solution and fixed in buffered 2% osmium tetroxide for one hour. The samples were then rinsed in the sodium cacodylate buffer solution, dehydrated using an ethanol series (50%, 70%, 80%, 90%, 95% and 100%) and critical point dried using liquid carbon dioxide. The dried samples were placed onto A1 SEM mounts with double stick tape and coated with Au/Pd using the Polaron E5100 Coating Unit for electron beam conductivity. The SEM analyses and micrographs were obtained using a JEOL 840 scanning electron microscope.

Example 1

The following porous biosupports have been prepared according to the process of the invention.

A porous biosupport designated R533 was prepared by blending a composition containing 67 wt. % nylon 6,6 (Vydyne®21 of Monsanto Company) and 33 wt. % chopped glass fibers ($\frac{1}{32}^2$ (0.32 cm) length; Certainteed 93B Fiberglass) using a twin-shell cone blender. The nylon had a moisture content of 0.3–0.5 wt. %, i.e. contained 0.3–0.5 wt. % water. The blend was compounded using a $1.5^2$ (3.8 cm) diameter, 24/1 L/D non-vented extruder at a temperature of about 285° C. (extruder barrel temperatures were set on a decreasing profile of 295–280° C.). The extrudate was quenched in a water bath and pelletized.

A porous biosupport designated 740FG was prepared according to the method used to prepare biosupport R533 except the nylon was a nylon 6,6 crumb containing finish oils and the extruder was a $1.5^2$ (3.8 cm) diameter, 24/1 L/D non-vented single screw extruder. The nylon 6,6 crumb was produced by chopping nylon 6,6 fibers (Monsanto Company) into $\frac{1}{16}$–$\frac{1}{8}$ inch (0.16–0.32 cm) lengths and passing through a Pallman densifier (Plas-Aglomerator). In this process, the nylon fibers were fused together via frictional heat and passed through a die to obtain the final crumb product.

A porous biosupport designated 744FG was prepared according to the method used to prepare biosupport 740FG except the nylon was a nylon 6,6 crumb without finish oils.

Biosupports R533, 740FG and 744FG were analyzed using mercury intrusion porosimetry to determine pore size distribution. In addition, the consolidated bulk density of the biosupports was determined. The results are set forth in Table I.

In addition, a $12^2$ (30.5 cm) packed bed of biosupport R533 submerged in water was completely fluidized by air injection into the bottom of a $3.5^2$ (8.9 cm) ID column indicating that periodic fluidization to remove excess microbial biomass could be done with air injection as opposed to more expensive and difficult hydraulic mixing and backflushing.

TABLE I

| Biosupport | Cumulative Pore Volume mL/g | Cumulative Pore Area m²/g | Mean Pore Dia.[a] $\mu$m | Pore Range[a] $\mu$m | Bulk Density lb/ft³ |
|---|---|---|---|---|---|
| R533 | 0.5 | 0.036 | 83.5 | 3–390 | 20.2 |
| 740 FG | 0.38 | 0.030 | 72.2 | 2–390 | 22. |
| 744 FG | 0.29 | 0.030 | 59.1 | 1–390 | 24. |

[a]As determined by mercury intrusion porosimetry where maximum pore size measurable is 390 $\mu$m.

Example 2

The following additional porous biosupports have been prepared according to the process of the invention.

A porous biosupport designated R400G was prepared by blending calcined clay (Englehard Corp., Satintone #5) and a nylon 6/6,6 random copolymer (Monsanto Company, 10.5 wt. % nylon 6 and 89.5 wt. % nylon 6,6). This blend was compounded by high intensity mixing in a Farrel Continuous Mixer. This mineral reinforced product was then blended with chopped glass fibers (described in Example 1) using a twin-shell cone blender (63.5 wt. % nylon, 20 wt. % clay and 16.5 wt. % glass fiber). The nylon contained 0.9 wt. % water. The blend was compounded using a $1.5^2$ (3.8 cm), 24/1 L/D non-vented single screw extruder at a temperature of 285° C. The extrudate was quenched in a water bath and pelletized.

A porous biosupport designated R400G-01 was prepared according to the method used for biosupport R400G except the composition also contained 0.2 wt. % carbon black (the carbon black was charged by adding 0.6 wt. % of a prepared carbon black concentrate containing 34 wt. % Cabot XC-72 carbon black in nylon 6 obtained from Custom Resins Incorporated (CRI).

A $12^2$ (30.5 cm) packed bed of porous biosupports R400G and R400G-01 were each submerged in water in the bottom of a $3.5^2$ (8.9 cm) ID column and fluidization with air attempted. Neither the R400G bed nor the R400G-01 bed was fluidized or mixed at the air injection rate which completely mixed the R533 biosupport. Low magnification light microscopy of the samples indicated that while R400G and R400G-01 were porous, R533 was more porous than either R400G or R400G-01. It is expected that R400G and R400G-01 could be fluidized at a higher air injection rate than that used for R533.

Example 3

The following additional porous biosupports containing fiber reinforcement and adsorbent material were prepared according to the process of the invention.

A porous biosupport designated T-4198 was prepared from nylon 6,6 crumb (Example 1) and 3 wt. % carbon black with 25 wt. % glass fiber reinforcement. A blend of 25 wt. % chopped glass fiber ($1/8^2$ (0.32 cm) length), 8.9 wt. % carbon black concentrate (34 wt. % carbon black in nylon 6; same concentrate as described in Example 2), and 66.1 wt. % nylon 6,6 crumb was prepared using a drum tumble blender. The nylon had a water content of 0.5–1.0 wt. %. The blend was compounded using a $1.5^2$ (3.8 cm) diameter, 24/1 L/D non-vented single screw extruder at a temperature of 285° C. The extrudate was quenched in a water bath and pelletized.

A porous biosupport designated T-4202 was prepared from the carbon black concentrate with 25 wt. % chopped glass fibers for reinforcement to yield 25.5 wt. % carbon black in the final product. A blend of 75 wt. % carbon black concentrate (34 wt. % carbon black in nylon 6; same concentrate as described in Example 2) and 25 wt. % chopped glass fiber ($1/8^2$ (0.32 cm) length) was prepared using a twin-shell cone blender. The concentrate had a water content of 0.5–1.0 wt. %. The blend was compounded using a $1.5^2$ (3.8 cm) diameter, 24/1 L/D non-vented single screw extruder at a temperature of 285° C. The extrudate was quenched in a water bath and pelletized.

Example 4

This example shows a comparison between porous nylon biosupport R533 of the invention and two commercial biosupports which are commonly used as supports for immobilized bacteria in bioreactors, i.e. R635 diatomaceous earth beads from Manville Company and activated coconut carbon from Charcoal Filtration Co.

Figure 1:
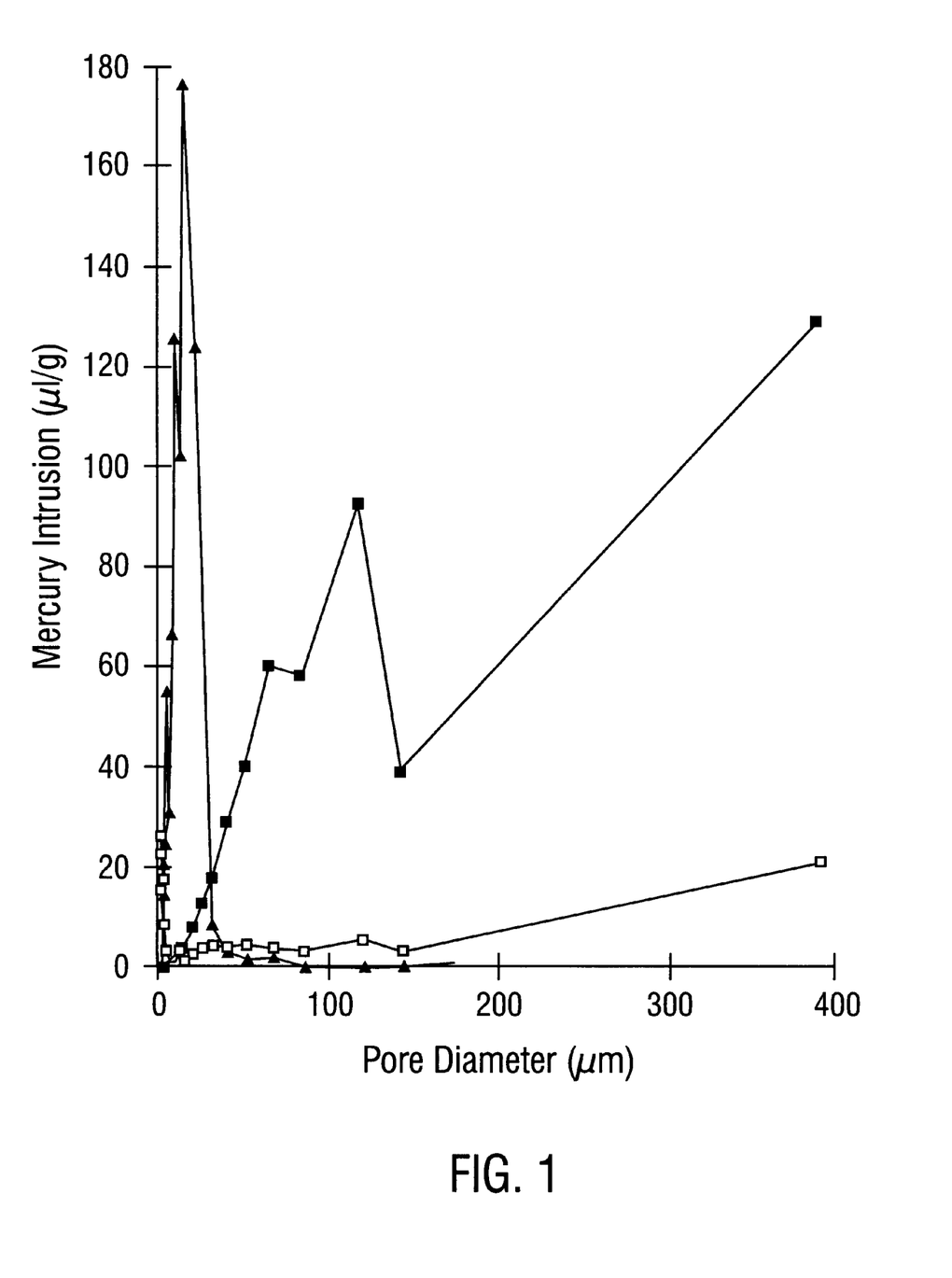
FIG. 1 is a plot of the incremental pore volume (measured as incremental intrusion of mercury into pores of specific pore sizes at various pressures during mercury intrusion porosimetry analysis) versus pore diameter for porous nylon biosupport R533 of the invention (designated by solid squares) compared to two conventional biosupports, i.e. diatomaceous earth beads (designated by solid triangles) and activated coconut carbon (designated by open squares). Each data point represents the pore volume for pores ranging in size from the plotted value down to the next lower plotted value.

Mercury intrusion porosimetry analyses were conducted on each sample. The R533 biosupport had a mean pore diameter of 83.5 $\mu$m while the R635 diatomaceous earth and activated coconut carbon biosupports had mean pore diameters of 12.9 $\mu$m and 0.113 $\mu$m, respectively. Incremental intrusion (measured in $\mu$L of pore volume per gram of biosupport) was plotted vs. pore diameter for the three samples (FIG. 1). FIG. 1 clearly shows the significant differences between the R533 porous biosupport of the invention and the R635 diatomaceous earth and activated coconut carbon biosupports. The R533 biosupport contains a significantly greater number of pores with pore diameter greater than 50 $\mu$m indicating that the porous biosupports of the invention should result in faster startup after inoculation and higher overall performance for chemical biodegradation. In addition, the open porosity of the porous biosupports of the invention should result in better penetration of chemical and oxygen into the interior of the particle resulting in higher overall levels of microbial activity in comparison to the conventional biosupports which have limited diffusion of chemical or oxygen.

Example 5

This example demonstrates the effectiveness of R533 porous nylon pellets as a biosupport for Pseudomonas sp. PNP1 in the biodegradation of PNP in a packed bed bioreactor.

A Pseudomonas sp. strain PNP1 that had been isolated from municipal sludge (see Heitkamp et al, "Biodegradation of p-Nitrophenol in an Aqueous Waste Stream by Immobilized Bacteria", *Appl. Environ. Microbiol.*, October 1990, pp. 2967–2973) was used as inoculum for the biosupports in these experiments. This Pseudomonas sp. is able to completely degrade PNP as a sole source of carbon and energy.

A synthetic PNP waste stream (pH 7.8) consisting of half strength inorganic mineral salts (L-salts) containing PNP concentrations ranging from 100 to 1400 mg/L was pumped though the immobilized bacteria columns to determine the performance of immobilized bacteria for degrading PNP.

The bench-scale PBRs in this study were 3.5 inch (8.9 cm) inside diameter×24 inch (61 cm) long×0.2 inch (0.5 cm) wall plexiglass columns. The columns used in the high-flow studies were 2.125 inch (5.4 cm) inside diameter×24 inch (61 cm) long×0.2 inch (0.5 cm) wall plexiglass tubes. The bottom of each column was sealed by a rubber stopper and a wire screen located 2.5 inches above the base supported a 12 inch bed depth of biosupport in each column. An air stone was inserted through the rubber stopper at the base to provide continuous aeration of each column and air was introduced at a flow rate of 750 cc/min for the 3.5 inch (8.9 cm) column and 300 cc/min for the 2.125 inch (5.4 cm) column. This aeration maintained oxygen saturation of liquid throughout the length of each column during the length of the experiment. The synthetic PNP waste stream was pumped into each column through a stainless steel tube located 1 inch (2.54 cm) above the bottom of the biosupport bed. The effluent from each column was discharged from a liquid headspace via a drain line positioned 2 inches (5.1 cm) above the top of the biosupport bed.

The R533 porous nylon biosupport was inoculated with a moderately turbid culture of Pseudomonas sp. strain PNP1 grown in half-strength L-salts containing 100 mg/L PNP. The L-salts were prepared according to Leadbetter, E. R. and Foster, J. W., "Studies on some methane utilizing bacteria", *Arch. Mikrobiol.*, 30:91 118 (1958). The purity of this culture was checked by selective plating on L-salts agar containing PNP, plating on standard plate count (SPC) agar and by direct examination with light microscopy. The porous nylon biosupport was inoculated by recycled pumping of a 1 liter turbid culture of Pseudomonas sp. strain PNP1 at 1 ml/min through the PBR bed for 24 hours with continuous aeration.

Once microbial degradation of PNP was observed in the PBR, synthetic wastes were pumped continuously through the PBR. Metered liquid pumps from FMI corporation (Model RHSY, Oyster Bay, N.Y.) were used to feed synthetic wastes into the PBR at calibrated flow rates throughout the study. Chemical loading to the columns was increased by raising the concentration of PNP in the feedstock to approximately 1,400 mg/L and increasing the feed rate to 2 ml/min. In the second phase of testing, the concentration of PNP was maintained at approximately 66 mg/L, but the flow rates were increased until continuous breakthrough of PNP was observed in the PBR effluent.

Figure 2:
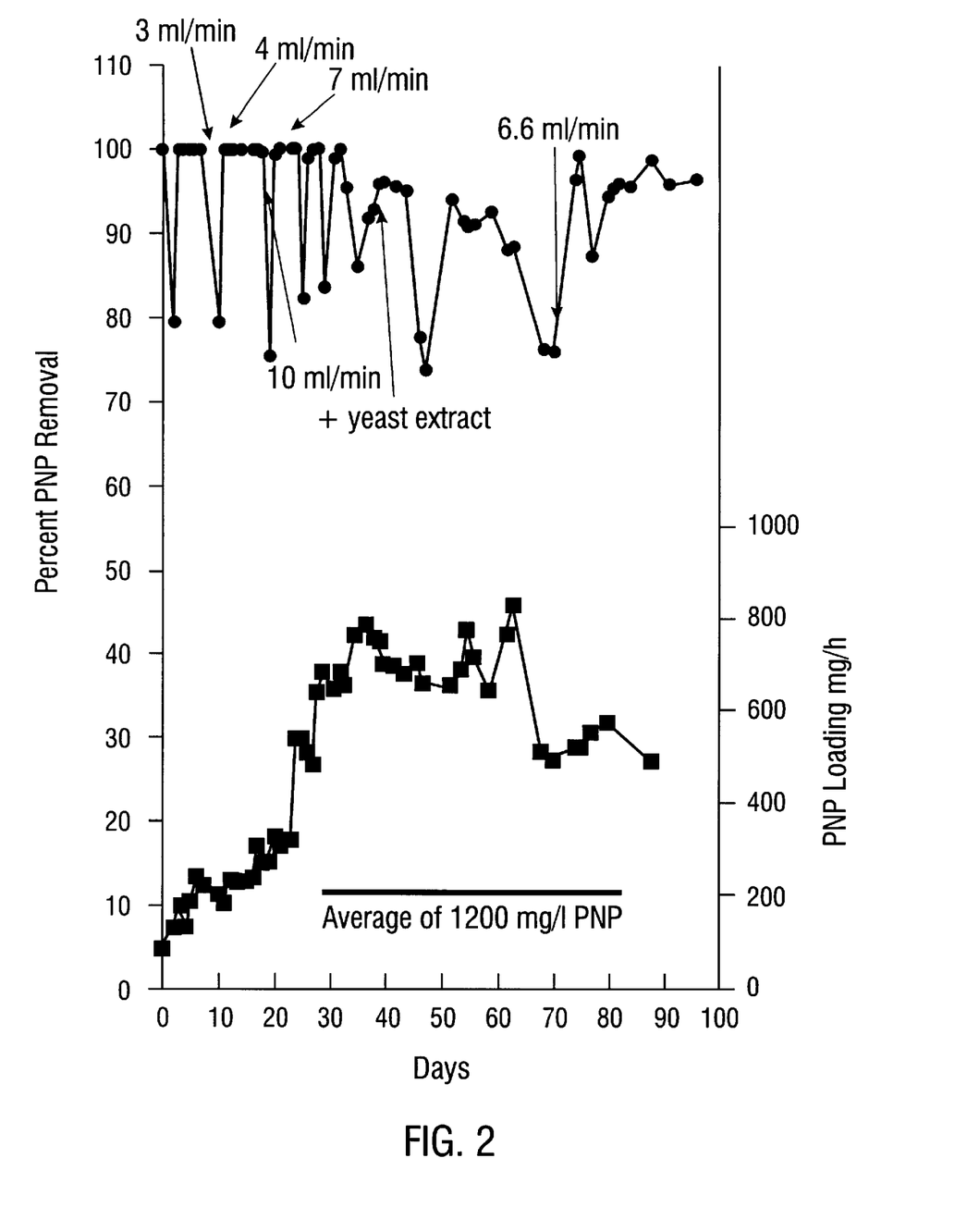
FIG. 2 is a plot of the biodegradation of p-nitrophenol at high chemical loading by Pseudomonas sp. PNP1 on R533 porous nylon biosupport in a PBR.

The biodegradation of PNP by Pseudomonas sp. PNP1 immobilized on R533 porous nylon pellets in the 3.5 inch (9.8 cm) PBR at increasing chemical loadings is shown in FIG. 2. The chemical loading of PNP (mg/h) into the PBR was raised by first increasing the concentration of PNP in the synthetic media from 400 mg/L to 1200 mg/L during the first 7 days of the experiment. Further increases in PNP loading were accomplished by step-wise increases in the feed flow rate from 3 ml/min up to 10 ml/min during days 15–25. Since significant levels of microbial biomass were observed on the porous nylon biosupport during the second week of operation, the packed bed was fluidized by vigorous air injection on day 19. This fluidization caused the release of the excess biomass into the PBR effluent and resulted in very little observable excess biomass in the PBR after fluidization. Therefore, the packed bed was fluidized approximately every other day throughout the remainder of the experiment to prevent liquid channeling or the loss of reactor volume due to accumulation of excess biomass in the PBR.

The biodegradation of PNP by immobilized bacteria in the PBR showed a pattern of 15–25% breakthrough of undegraded PNP within 24 h after each step increase in chemical loading. Characteristically, the PBR would regain a high rate of PNP biodegradation within the next 24–48 hours. Presumably, this recovery resulted from further growth of bacteria into the biosupport in the PBR in response to each increase in chemical loading. However, consistent breakthrough of undegraded PNP was observed in the PBR effluent after day 33 when PNP loading was increased sharply from 657 mg/hr to 787 mg/hr. The removal of PNP dropped initially to 86% and recovered to 91–96% removal over the next 10 days (days 35–44) as PNP loading averaged 736 mg/hr. The performance of the PBR unexpectedly dropped to 74–77% removal on days 46–47. Since chemical loading had not increased in this time frame, the PBR did not contain excess biomass and no operational problems were evident, it was presumed that the immobilized bacteria were stressed by a lack of micronutrients or trace elements due to long exposure to synthetic feed containing only inorganic macronutrients and PNP. The addition of 5 mg/L of yeast extract, a common source of micronutrients and trace elements, restored performance. Throughout the remainder of the experiment the synthetic feed was supplemented with 5–10 mg/L of yeast extract to eliminate micronutrient limitation as an experimental variable. The PBR averaged 91% PNP removal during the eleven day period from days 52–62 when PNP loading averaged 707 mg/hr and 95.3% PNP removal from days 74–96 (22 days) when PNP loading averaged 532 mg/hr.

Figure 3:
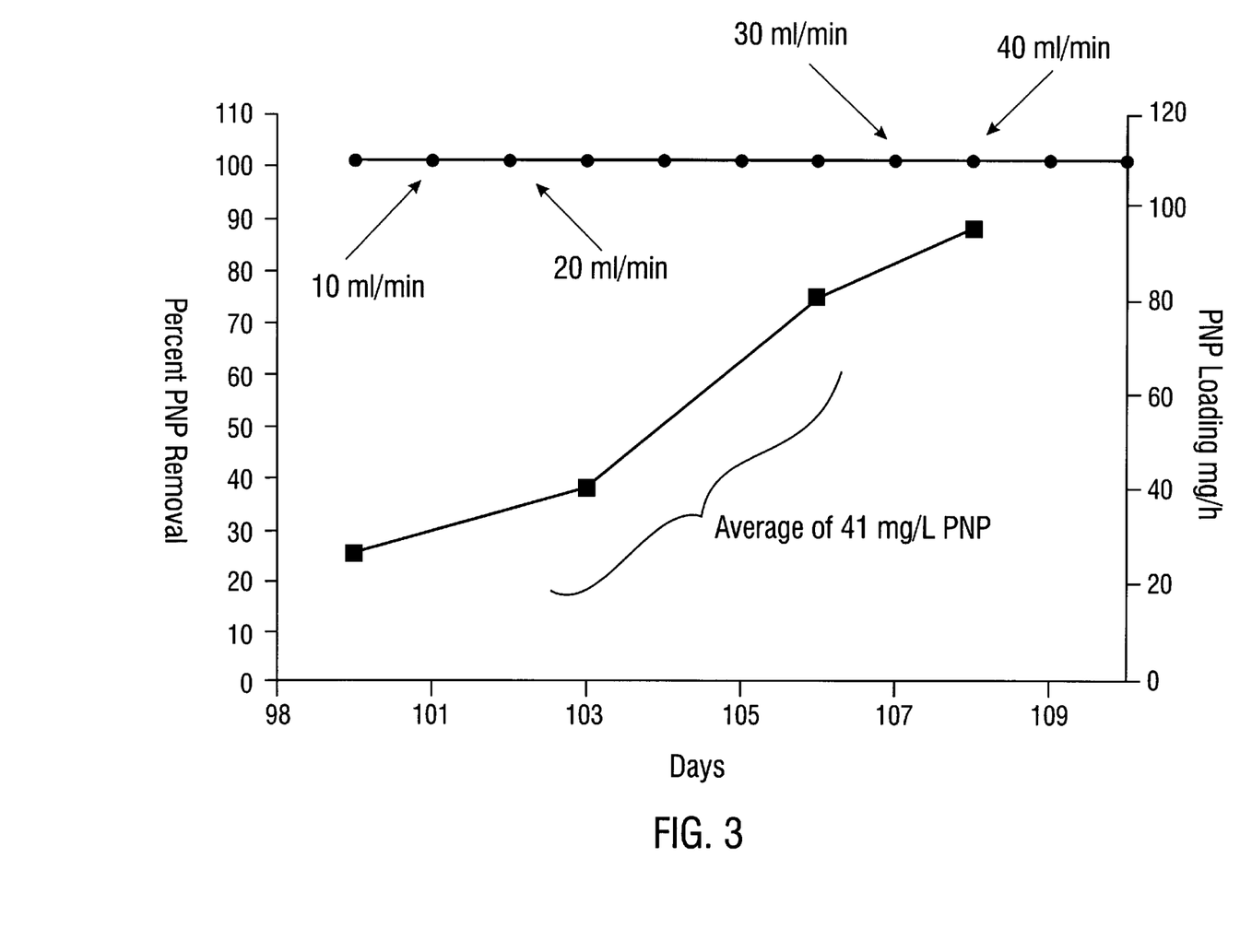
FIG. 3 is a plot of the biodegradation of p-nitrophenol at high flow rates by Pseudomonas sp. PNP1 on R533 porous nylon biosupport in a 3.5 inch (8.9 cm) inside diameter PBR.
Figure 4:
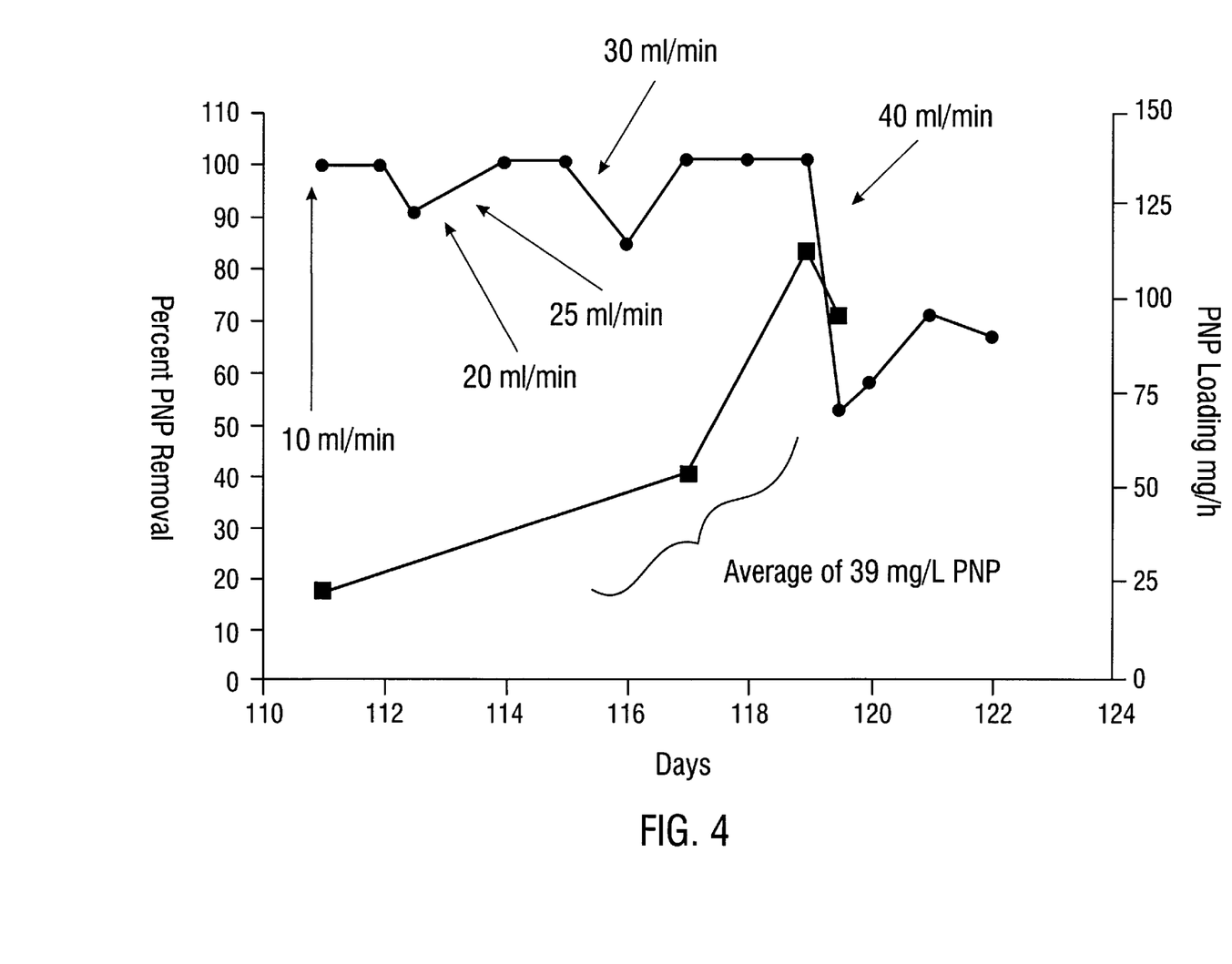
FIG. 4 is a plot of the biodegradation of p-nitrophenol at high flow rates by Pseudomonas sp. PNP1 on R533 porous nylon biosupport in a 2.125 inch (5.4 cm) inside diameter PBR.
Figure 5A:
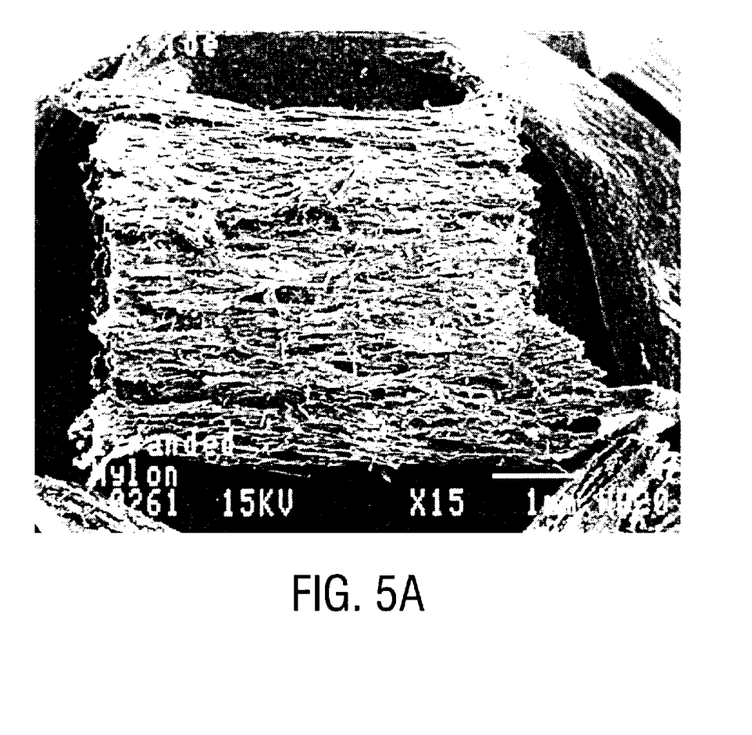
FIGS. 5A and 5B are longitudinal surface views of the R533 porous nylon biosupport at two different magnifications.
Figure 5B:
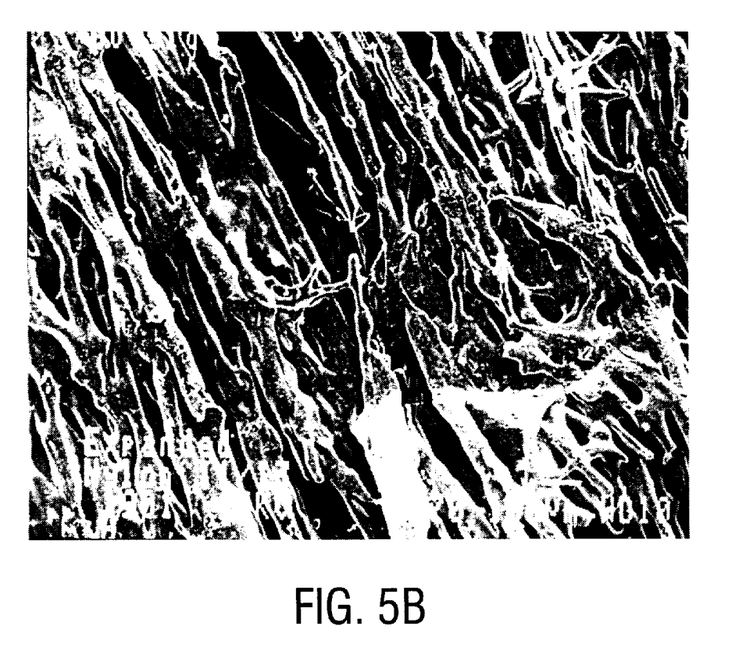

The performance of bacteria immobilized on R533 porous nylon pellets were also evaluated for high-flow applications. The concentration of PNP in the synthetic feed was dropped to approximately 40 mg/L and the flow was increased stepwise through the PBR until consistent breakthrough of undegraded PNP was observed in the effluent (FIG. 3). However, flow rates as high as 40 ml/min failed to result in any detectable discharge of undegraded PNP. Since higher flow rates were impractical in the laboratory due to the high volume of feed required, a portion of the porous nylon was transferred from the 3.5 inch (8.9 cm) inside diameter column to a column having a 2.125 inch (5.4 cm) inside diameter. This significantly lowered the volume of the PBR resulting in shorter hydraulic residence times for the same flows tested in the larger column. The smaller PBR maintained near complete PNP removal at flow rates of 10, 20, 25 and 30 mls/min, but dropped to 51–69% removal at 40 ml/min on days 119–122 (FIG. 4).

Table II shows a summary of the maximum chemical degradation rates for high chemical concentration and high liquid flow applications of Pseudomonas sp. PNP1 immobilized on porous nylon R533 biosupport in the PBR. In both cases, the Pseudomonas sp. PNP1 immobilized on porous nylon R533 biosupport removed >90% of the PNP.

TABLE II

Maximum Chemical Degradation Rates for Pseudomonas sp. PNP1 immobilized on porous nylon R533 biosupport in the PBR

| Mean PNP[a] Concentration (mg/L) | Hydraulic Residence Time (min) | PNP Removal (%) | PNP Removed (lb/ft³/day) | COD Removed (lb/ft³/day) |
|---|---|---|---|---|
| 40 | 12 | >99 | 0.18 | 0.32 |
| 1200 | 130 | 90+ | 0.37 | 0.66 |

[a]p-Nitrophenol in synthetic L-salts medium.

A sample of the biofilm from the biosupport bed in the PBR at the conclusion of the chemical loading study was plated onto petri dishes containing SPC media and 2% agar. Bacterial isolates were selected from the SPC plates based upon observed differences in pigmentation, colony morphology, cellular morphology and grain reaction. The isolates were transferred to agar plates containing 100 mg/L PNP. Isolates capable of degrading PNP were determined by observing clearing of the yellow PNP surrounding the colony. The isolated bacteria were incubated for 24 hours on Trypticase Soy Agar prior to identification using a VITEK AMS microbial identification system (McDonnel Douglas Inc., St. Louis, Mo.). Cellular morphology and gram stain were determined with an Axioskop light microscope (Zeiss, Federal Republic of Germany). One major bacterial morphotype was isolated from the R533 porous nylon biosupport at the conclusion of these experiments. This microorganism was identified as a Pseudomonas sp. by the VITEK AMS microbial identification system and was presumed to be the Pseudomonas sp. PNPI originally inoculated onto the porous nylon biosupport.

Example 6

The R533 porous nylon biosupport produced according to the process of the invention was analyzed for the presence of macropores using scanning electron microscopy.

Figure 6A:
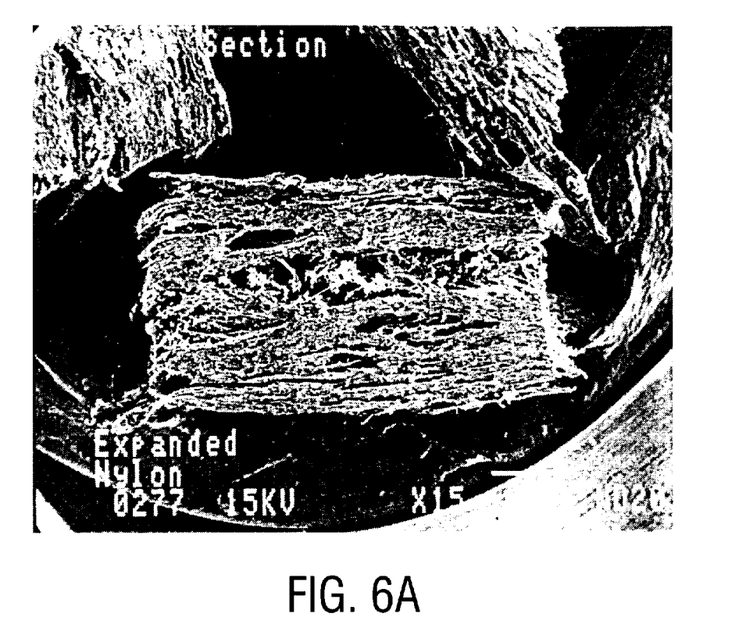
FIGS. 6A and 6B are longitudinal cross section views of the R533 porous nylon biosupport at two different magnifications.
Figure 6B:
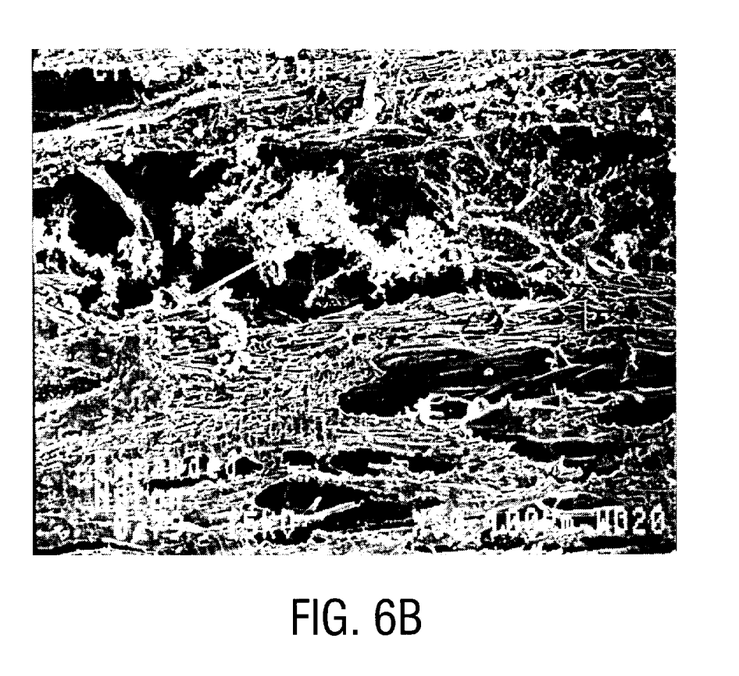
Figure 7:
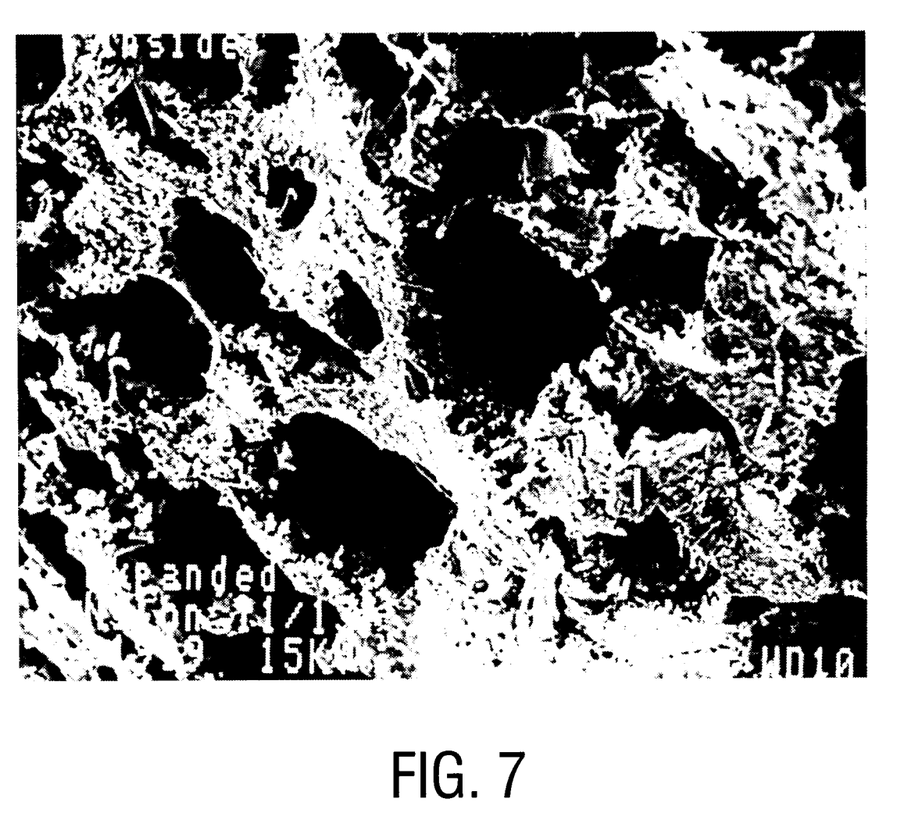
FIG. 7 is an end view of the R533 porous nylon biosupport.

Micrographs of the R533 porous nylon biosupport were taken in three views: longitudinal surface (FIG. 5), longitudinal cross section (FIG. 6), and end view (FIG. 7).

The longitudinal surface view at 15× magnification (FIG. 5A) shows the rough fibrous characteristics of the surface of the extruded porous nylon biosupport. The surface structure appears rough and irregular in texture and numerous large openings provide for microbial penetration, attachment and growth.

The longitudinal surface at 70× magnification (FIG. 5B) more clearly shows the large openings in the surface of the fibrous polymer biosupport. It is noteworthy that some large openings, ranging in size from 20–700 $\mu$M, are seen to extend from the longtidunal surface down into the interior of the porous biosupport thus providing ready internal access to inoculated bacteria.

The longitudinal cross sectional view at 15× magnification (FIG. 6A) shows that extremely large pore openings exist throughout the inside of the biosupport running in parallel to the direction of extrusion. It is noteworthy that many of these cavities are 800–1200 $\mu$M in length and some are as long as 3.9 mm. These cavities allow the existence of large populations of chemical-degrading bacteria within the biosupport. Furthermore, the open structured matrix of the biosupport eliminates growth limitations due to slow diffusion of nutrients or chemical into the biosupport.

The longitudinal cross section view at 50× magnification (FIG. 6B) more clearly shows the size and shape of these large internal cavities. The diameters of these long cavities range from 30–690 $\mu$M with most having a diameter of 95–295 $\mu$M.

The end-view at 70× magnification (FIG. 7) shows that the long cavities running through the porous biosupport (as seen in FIG. 6A and 6B) exist as open channels and are accessed through openings in the cut end of the biosupport. These openings are numerous across the end of the biosupport and have diameters ranging from 40–415 $\mu$M providing ready access to inoculated bacteria.

It is clear from these scanning electron microscopy analyses that the porous nylon biosupport contains a high number of very large pore openings. Furthermore, these pore openings occur throughout the interior of the biosupport and are accessible to microorganisms by openings through both the sides and cut ends of the biosupport.

What is claimed is:

1. A composition for the biotreatment of an aqueous waste stream comprising microorganisms colonized within the pores of a porous biosupport, said biosupport comprising:
   (a) 40–100 wt. % of a polymeric material comprising a polymer selected from the group consisting of nylon, thermoplastic polyester, ethylene-vinyl acetate copolymer, ethylene-vinyl alcohol copolymer, polysulfone, polyolefin, polyvinyl chloride, polycarbonate, polyimide, polyetheretherketone, polyphenylene sulfide, cellulose ester plastics, polyvinyl butyral, styrenic polymers, rigid, thermoplastic polyurethanes, and mixtures thereof;
   (b) 0–60 wt. % of a fiber reinforcement;
   (c) 0–60 wt. % of an adsorbent material; and
   (d) 0–40 wt. % of an inorganic filler,
wherein the sum of the amounts of fiber reinforcement, adsorbent material and inorganic filler in said biosupport is 0–60 wt. %, and wherein said biosupport has a specific gravity greater than the specific gravity of water and pores of sufficient diameter to enable microorganisms to colonize within the pores.

2. The composition of claim 1 wherein the pores of said biosupport have a diameter in the range of 1 $\mu$m to about 700 $\mu$m.

3. The composition of claim 2 wherein said pores have a median diameter (based on volume) of at least about 40 $\mu$m for pore sizes in the range of 1 $\mu$m to 390 $\mu$m.

4. The composition of claim 3 wherein said pores have a volume of at least about 0.2 mL/g for pore sizes in the range of 1 $\mu$m to 390 $\mu$m.

5. The composition of claim 1 wherein said polymeric material comprises a polymer selected from the group consisting of nylon, thermoplastic polyester, ethylene-vinyl alcohol copolymer, polysulfone, polyvinyl chloride, polycarbonate, polyimide, polyetheretherketone, polyphenylene sulfide, cellulose ester plastics, polyvinyl butyral, styrenic polymers, rigid, thermoplastic polyurethanes, and mixtures thereof.

6. The composition of claim 5 wherein said polymeric material comprises nylon.

7. The composition of claim 1 comprising about 5 to about 50 wt. % of a fiber reinforcement.

8. The composition of claim 7 comprising about 15 to about 40 wt. % of a fiber reinforcement.

9. The composition of claim 7 comprising about 2 to about 50 wt. % of an adsorbent material.

10. The composition of claim 1 comprising 40 to about 80 wt. % of said polymeric material.

11. The composition of claim 7 comprising about 5 to about 30 wt. % of an inorganic filler.

12. The composition of claim 6 wherein said polymeric material further comprises material selected from the group consisting of polyolefin, styrene-butadiene rubber, an inorganic filler and mixtures thereof.

13. The composition of claim 6 wherein said nylon is selected from the group consisting of nylon 6, nylon 6,6, nylon 4,6, nylon 12, nylon 11, nylon 6,9, nylon 6,10, and blends or copolymers thereof.

14. The composition of claim 11 wherein said polymeric material contains about 35 to about 95 wt. % nylon.

15. The composition of claim 1 wherein said polymeric material consists essentially of nylon.

16. The composition of claim 1 wherein said fiber reinforcement is fibers selected from the group consisting of glass, carbon, aramid, fiber-forming inorganic material selected from alumina, silica, wollastonite, boron, boron nitride, boron carbide, silicon carbide or alumino-silicate and mixtures thereof.

17. The composition of claim 16 wherein said fiber reinforcement is chopped fibers.

18. The composition of claim 16 wherein said fiber reinforcement is glass fiber or carbon fiber.

19. The composition of claim 1 wherein said adsorbent material is selected from the group consisting of carbon, ion exchange resins, zeolites and mixtures thereof.

20. The composition of claim 19 wherein said adsorbent material is charcoal or activated carbon.

21. A process for preparing a porous biosupport comprising extruding in a non-vented extruder a composition comprising:
   (a) 40–100 wt. % of a polymeric material comprising a polymer selected from the group consisting of nylon, thermoplastic polyester, ethylene-vinyl acetate copolymer, ethylene-vinyl alcohol copolymer, polysulfone, polyolefin, polyvinyl chloride, polycarbonate, polyimide, polyetheretherketone, polyphenylene sulfide, cellulose ester plastics, polyvinyl butyral, styrenic polymers, rigid, thermoplastic polyurethanes, and mixtures thereof;
   (b) 0–60 wt. % of a fiber reinforcement;
   (c) 0–60 wt. % of an adsorbent material; and
   (d) 0–40 wt. % of an inorganic filler,
wherein the sum of the amounts of fiber reinforcement, adsorbent material and inorganic filler in said biosupport is 0–60 wt. %, in the presence of about 0.1 to about 7 wt. % of water, a foaming agent or mixtures thereof, and pelletizing the extrudate from said extruder; wherein said biosupport has a specific gravity greater than the specific gravity of water and pores of sufficient diameter to enable microorganisms to colonize within the pores.

22. The process of claim 21 wherein the amount of water, foaming agent or mixture thereof present is about 0.1 to about 5 wt. %.

23. The process of claim 21 wherein said biosupport has pores having a diameter in the range of 1 $\mu$m to about 700 $\mu$m.

24. The process of claim 23 wherein said biosupport has pores having a median pore diameter (based on volume) of at least about 40 $\mu$m for pore sizes in the range of 1 $\mu$m to 390 $\mu$m.

25. The process of claim 24 wherein said biosupport has pores having a pore volume of at least about 0.2 mL/g for pore sizes in the range of 1 $\mu$m to 390 $\mu$m.

26. The process of claim 21 wherein said polymeric material comprises a polymer selected from the group consisting of nylon, thermoplastic polyester, ethylene-vinyl alcohol copolymer, polysulfone, polyvinyl chloride, polycarbonate, polyimide, polyetheretherketone, polyphenylene sulfide, cellulose ester plastics, polyvinyl butyral, styrenic polymers, rigid, thermoplastic polyurethanes, and mixtures thereof.

27. The process of claim 26 wherein said polymeric material comprises nylon.

28. The process of claim 21 wherein said biosupport comprises about 5 to about 50 wt. % of a fiber reinforcement.

29. The process of claim 28 wherein said biosupport comprises about 2 to about 50 wt. % of an adsorbent material.

30. The process of claim 28 comprising about 5 to about 30 wt. % of an inorganic filler.

31. The process of claim 27 wherein said polymeric material in said biosupport further comprises material selected from the group consisting of polyolefin, styrene-butadiene rubber, an inorganic filler and mixtures thereof.

32. The process of claim 31 wherein said polymeric material contains about 35 to about 95 wt. % nylon.

33. The process of claim 21 wherein said polymeric material of said biosupport consists essentially of nylon.

34. The process of claim 27 wherein said nylon in said biosupport is selected from the group consisting of nylon 6, nylon 6,6, nylon 4,6, nylon 11, nylon 12, nylon 6,9, nylon 6,10, and blends or copolymers thereof.

35. The process of claim 21 wherein said foaming agent is fluorinated aliphatic hydrocarbons, 1,1-azobisformamide, p,p'-oxybis-(benzenesulfonyl hydrazide), p-toluene sulfonyl semicarbazide, trihydrazine triazine, 5-phenyltetrazole, sodium bicarbonate and mixtures thereof.

36. The process of claim 21 wherein said composition is extruded in the presence of water.

37. The process of claim 21 wherein said composition further comprises an amount of a polymeric additive material wherein said additive material contains one or more of said fiber reinforcement, adsorbent material, inorganic fillers, and polymeric material in addition to a plastic or rubber material not suitable as the polymeric material (a) of said composition and wherein the amount of said plastic or rubber material plus the amount of any additives other than said fiber reinforcement, adsorbent material and inorganic filler present in said composition is up to about 25 wt. %.

38. The biosupport of claim 1 wherein said biosupport further comprises an amount of a polymeric additive material wherein said additive material contains one or more of said fiber reinforcement, adsorbent material, inorganic fillers, and polymeric material in addition to a plastic or rubber material not suitable as the polymeric material (a) of said biosupport and wherein the amount of said plastic or rubber material plus the amount of any additives other than said fiber reinforcement, adsorbent material and inorganic filler present in said biosupport is up to about 25 wt. %.

39. The process of claim 21 wherein the amount of water, foaming agent, or mixture thereof is about 0.1 to about 2 wt. %.

40. The process of claim 21 wherein the amount of water, foaming agent, or mixture thereof is about 0.2 to about 1 wt. %.

* * * * *

UNITED STATES PATENT AND TRADEMARK OFFICE
CERTIFICATE OF CORRECTION

PATENT NO. : 5,980,738

DATED : November 9, 1999

INVENTOR(S) : Heitkamp et al.

It is certified that error appears in the above-identified patent and that said Letters Patent is hereby corrected as shown below:

Column 3, line 33, after "magnification" please insert --(scanned images)--

Column 3, line 36, after "magnification" please insert --(scanned images)--

Column 3, line 39, after "biosupport" please insert --(scanned image)--

Signed and Sealed this

Fifth Day of December, 2000

Attest:

Q. TODD DICKINSON

*Attesting Officer*     *Director of Patents and Trademarks*